USO05534494A

United States Patent [19]

Bowers et al.

[11] Patent Number: 5,534,494

[45] Date of Patent: Jul. 9, 1996

[54] POLYPEPTIDE COMPOUNDS HAVING GROWTH HORMONE RELEASING ACTIVITY

[75] Inventors: Cyril Y. Bowers, New Orleans, La.; Frank A. Momany, Concord, Mass.; Ching H. Chang; Wayne L. Cody, both of Kingsport, Tenn.; John C. Hubbs, Gray; Charles H. Foster, Kingsport, both of Tenn.

[73] Assignee: Polygen Holding Corporation, Wilmington, Del.

[21] Appl. No.: 231,986

[22] Filed: Apr. 21, 1994

Related U.S. Application Data

[63] Continuation of Ser. No. 880,284, May 4, 1992, abandoned, which is a continuation of Ser. No. 770,710, Oct. 3, 1991, abandoned, which is a continuation of Ser. No. 149,267, Jan. 28, 1988, abandoned.

[51] Int. Cl.⁶ .......................... A61K 38/00; A61K 38/02; C07K 5/00; C07K 7/00
[52] U.S. Cl. .......................... 514/16; 514/15; 530/329; 530/328; 530/327
[58] Field of Search ............... 514/15, 16; 530/327–330, 530/329

[56] References Cited

U.S. PATENT DOCUMENTS

| 4,061,626 | 12/1977 | Shields . |  |
|---|---|---|---|
| 4,105,603 | 8/1978 | Vale, Jr. et al. . |  |
| 4,127,517 | 11/1978 | Coy et al. . |  |
| 4,127,518 | 11/1978 | Coy et al. . |  |
| 4,127,519 | 11/1978 | Coy et al. . |  |
| 4,127,520 | 11/1978 | Coy et al. . |  |
| 4,127,521 | 11/1978 | Coy et al. . |  |
| 4,127,522 | 11/1978 | Coy et al. . |  |
| 4,127,523 | 11/1978 | Coy et al. . |  |
| 4,127,524 | 11/1978 | Coy et al. . |  |
| 4,127,525 | 11/1978 | Coy et al. . |  |
| 4,127,526 | 11/1978 | Coy et al. . |  |
| 4,127,527 | 11/1978 | Coy et al. . |  |
| 4,127,528 | 11/1978 | Coy et al. . |  |
| 4,127,529 | 11/1978 | Coy et al. . |  |
| 4,127,530 | 11/1978 | Coy et al. . |  |
| 4,127,531 | 11/1978 | Coy et al. . |  |
| 4,127,532 | 11/1978 | Coy et al. . |  |
| 4,127,533 | 11/1978 | Coy et al. . |  |
| 4,127,534 | 11/1978 | Coy et al. . |  |
| 4,127,535 | 11/1978 | Coy et al. . |  |
| 4,127,536 | 11/1978 | Coy et al. . |  |
| 4,127,537 | 11/1978 | Coy et al. . |  |
| 4,127,538 | 11/1978 | Coy et al. . |  |
| 4,127,539 | 11/1978 | Coy et al. . |  |
| 4,127,540 | 11/1978 | Coy et al. . |  |
| 4,127,541 | 11/1978 | Coy et al. . |  |
| 4,139,504 | 2/1979 | Coy et al. . |  |
| 4,178,284 | 12/1979 | Sarantakis . |  |
| 4,211,693 | 7/1980 | Rivier et al. . |  |
| 4,218,474 | 8/1980 | Barnish . |  |
| 4,223,019 | 9/1980 | Momany . |  |
| 4,223,020 | 9/1980 | Momany . |  |
| 4,223,021 | 9/1980 | Momany . |  |
| 4,224,316 | 9/1980 | Momany . |  |
| 4,226,857 | 10/1980 | Momany . |  |
| 4,228,155 | 10/1980 | Momany . |  |
| 4,228,156 | 10/1980 | Momany . |  |
| 4,228,157 | 10/1980 | Momany . |  |
| 4,228,158 | 10/1980 | Momany . |  |
| 4,312,857 | 1/1982 | Coy et al. . |  |
| 4,316,891 | 2/1982 | Guillemin et al. . |  |
| 4,350,627 | 9/1982 | de Castiglione et al. . |  |
| 4,372,884 | 2/1983 | Brown et al. . |  |
| 4,393,050 | 7/1983 | Vale, Jr. et al. . |  |
| 4,410,512 | 10/1983 | Bowers . |  |
| 4,410,513 | 10/1983 | Momany . |  |
| 4,411,890 | 10/1983 | Momany . |  |
| 4,428,942 | 1/1984 | Rivier et al. . |  |
| 4,491,541 | 1/1985 | de Castiglione et al. . |  |
| 4,505,897 | 3/1985 | Coy et al. | 514/11 |
| 4,508,711 | 4/1985 | Coy et al. | 514/11 |
| 4,517,181 | 5/1985 | Ling et al. | 514/12 |
| 4,518,586 | 5/1985 | Rivier et al. | 514/12 |
| 4,528,190 | 7/1985 | Vale, Jr. et al. | 514/12 |
| 4,529,595 | 7/1985 | Rivier et al. | 514/12 |
| 4,562,175 | 12/1985 | Chang et al. | 514/12 |
| 4,563,352 | 1/1986 | Rivier et al. | 514/12 |
| 4,585,756 | 4/1986 | Brazeau, Jr. et al. | 514/12 |
| 4,595,676 | 6/1986 | Spiess et al. | 514/12 |
| 4,605,643 | 8/1986 | Bohlen et al. | 514/12 |
| 4,610,976 | 9/1986 | Bohlen et al. | 514/12 |
| 4,617,149 | 10/1986 | DiMarchi et al. | 530/324 |
| 4,622,312 | 11/1986 | Felix et al. | 514/12 |
| 4,626,523 | 12/1986 | Vale, Jr. et al. | 514/12 |
| 4,628,043 | 12/1986 | Spiess et al. | 514/12 |
| 4,649,131 | 3/1987 | Felix et al. | 514/12 |
| 4,839,344 | 6/1989 | Bowers | 530/324 |
| 4,880,778 | 11/1989 | Bowers | 514/12 |

FOREIGN PATENT DOCUMENTS

| 0018072 | 10/1980 | European Pat. Off. . |
| 0083864 | 7/1983 | European Pat. Off. . |
| 0211267 | 2/1987 | European Pat. Off. . |
| 8706835 | 11/1987 | WIPO . |
| 8809780 | 12/1988 | WIPO . |

OTHER PUBLICATIONS

Maier et al., *Experientia*, 32 (2), 246–248, 1975.

Primary Examiner—Christina Y. Chan
Assistant Examiner—A. M. Davenport
Attorney, Agent, or Firm—Ronald I. Eisenstein

[57] ABSTRACT

Disclosed are novel polypeptide compounds which promote the release and elevation of growth hormone levels in the blood of animals. Also disclosed are methods of promoting the release and elevation of growth hormone levels in the blood of animals using the disclosed polypeptide compounds.

9 Claims, No Drawings

POLYPEPTIDE COMPOUNDS HAVING GROWTH HORMONE RELEASING ACTIVITY

This is a continuation of application Ser. No. 07/880,284 filed on May 4, 1992 and now abandoned, which is a continuation of Ser. No. 07/770,710, filed Oct. 3, 1991 and now abandoned, which is a continuation of Ser. No. 07/149,267, filed Jan. 28, 1988 and now abandoned.

This invention relates to novel polypeptide compounds which promote the release of growth hormone when administered to animals. In another aspect, this invention relates to methods for promoting the release and elevation of growth hormone levels in animals by administration of specified growth hormone releasing polypeptide compounds thereto.

BACKGROUND OF THE INVENTION

It has been established in the scientific literature that the elevation of growth hormone (GH) levels in mammals upon administration of GH-releasing compounds can lead to enhanced body weight and to enhanced milk production if sufficiently elevated GH levels occur upon administration. Further, it is known that the elevation of growth hormone levels in mammals can be accomplished by application of known growth hormone releasing agents, such as the naturally occurring growth hormone releasing hormones.

The elevation of growth hormone levels in mammals can also be accomplished by application of growth hormone releasing peptides, some of which have been previously described, for example, by F. A. Momany in U.S. Pat. No. 4,223,019, U.S. Pat. No. 4,223,020, U.S. Pat. No. 4,223,021, U.S. Pat. No. 4,224,316, U.S. Pat. No. 4,226,857, U.S. Pat. No. 4,228,155, U.S. Pat. No. 4,228,156, U.S. Pat. No. 4,228,157, U.S. Pat. No. 4,228,158, U.S. Pat. No. 4,410,512 and U.S. Pat. No. 4,410,513.

Antibodies to the endogenous growth hormone release inhibitor, somatostatin (SRIF) have also been used to cause elevated GH levels. In this latter example, growth hormone levels are elevated by removing the endogenous GH-release inhibitor (SRIF) before it reaches the pituitary, where it inhibits the release of GH.

Each of these methods for promoting the elevation of growth hormone levels involve materials which are expensive to synthesize and/or isolate in sufficient purity for administration to a target animal. Short chain, relatively simple polypeptides which have the ability to promote the release of growth hormone would be desirable because they should be readily and inexpensively prepared, easily modified chemically and/or physically, as well as readily purified and formulated; and they should have excellent transport properties.

OBJECTS OF THE INVENTION

It is, therefore, an object of the present invention to provide novel growth hormone releasing compounds which are capable of promoting the release and elevation of growth hormone levels in the blood of animals.

It is another object of the present invention to provide methods for promoting the release and/or elevation of growth hormone levels in the blood of animals.

These and other objects of the present invention will become apparent from inspection of the following description and claims.

STATEMENT OF THE INVENTION

In accordance with the present invention, we have discovered several novel polypeptide compounds which promote the release of growth hormone in animals. The preparation, characterization and administration of these novel growth hormone releasing compounds will now be described in greater detail.

DETAILED DESCRIPTION OF THE INVENTION

The present invention is based on the discovery of several short chain (i.e., seven up to eleven amino acid residues) polypeptides which promote the release and elevation of growth hormone levels in the blood of animals. The polypeptides contemplated to be within the scope of the present invention are defined by the following generic structure:

wherein X is selected from the group consisting of:
His—AA1—,
3(NMe)His—AA1— (i.e., wherein the imidazole ring is methylated at the 3-position); wherein AA1 is selected from the group consisting of all naturally occurring L-amino acids and DAla;
AA0—His—AA1; and
AA0—3(NMe)His—AA1; wherein AA0 is selected from the group consisting of all naturally occurring L-amino acids, Met(O), DOPA and Abu; and AA1 is as defined above;

AA2 is selected from the group consisting of DPhe, DTrp, 5-fluoro-D or LTrp; 6-fluoro-D or LTrp (i.e., wherein the indole ring is fluorinated at the 5- or 6-position), (formyl)DTrp (i.e., DTrp which is formylated at the Indole nitrogen), *XTrp, wherein *XTrp is selected from the group consisting of the N-monomethylated DTrp isomers (i.e., (N$^\alpha$Me)DTrp and (indole NMe)DTrp), D$^\alpha$Nal and D$^\beta$Nal;

AA3 is selected from the group consisting of Ala, Gly and Ser;

AA5 is selected from the group consisting of DPhe and (NMe)DPhe;

Y is selected from the group consisting of:
(a) AA7, wherein AA7 is selected from the group consisting of Arg, iLys, Lys and Orn; and
(b) —AA6—AA7, wherein AA6 is selected from the group consisting of all naturally occurring L-amino acids, dipeptides of the naturally occurring L-amino acids, e.g., Ala—Ala, and compounds of the formula:

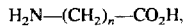

wherein n=1–12, and wherein AA7 is as defined above; and
Z represents the C terminal end group of said polypeptide or the C terminal amino acid(s) plus end group, wherein Z is selected from the group consisting of —CONH$_2$, —COOH, —COOR, —CONHR, —CONR$_2$, —CH$_2$OH and —CH$_2$OR, wherein R is an alkyl group having 1–6 carbon atoms or an aromatic ring having up to 12 carbon atoms; and wherein Z is alternatively selected from the group consisting of —Gly—Z', —Met—Z', —Lys—Z', —Cys—Z', —Gly—Tyr—Z', and —Ala—Tyr—Z', wherein Z' is selected from the group consisting of —CONH$_2$, —CONHR, —COOH, —COOR, —CONR$_2$, —CH$_2$OH, and —CH$_2$OR, wherein R is as defined above;

and organic or inorganic addition salts of any of said polypeptides;

wherein the amino acid residue abbreviations used are in accordance with the standard peptide nomenclature:

Gly= Glycine
Tyr= L-Tyrosine
Ile= L-Isoleucine
Glu= L-Glutamic Acid
Thr= L-Threonine
Phe= L-Phenylalanine
Ala= L-Alanine
Lys= L-Lysine
Asp= L-Aspartic Acid
Cys= L-Cysteine
Arg= L-Arginine
Gln= L-Glutamine
Pro= L-Proline
Leu= L-Leucine
Met= L-Methionine
Ser= L-Serine
Asn= L-Asparagine
His= L-Histidine
Trp= L-Tryptophan
Val= L-Valine
DOPA= 3,4-Dihydroxyphenylalanine
Met(O)= Methionine Sulfoxide
Abu=α-Aminobutyric Acid
iLys= $N^\epsilon$-Isopropyl-L-Lysine
4-Abu= 4-Aminobutyric Acid
Orn= L-Ornithine
$D^\alpha$Nal= α-Naphthyl-D-Alanine
$D^\beta$Nal= β-Naphthyl-D-Alanine All three letter amino acid abbreviations preceded by a "D" indicate the D-configuration of the amino acid residue. For purposes of this disclosure, glycine is considered to be included in the term "naturally occurring L-amino acids."

The flexibility associated with the choice of basic, neutral or acidic amino acid residues for amino acids X, AA2, AA3, AA5 and Y provides one with a great deal of control over the physiochemical properties of the desired peptide. Such flexibility provides important advantages for the formulation and delivery of the desired peptide to any given species. Additional flexibility can be imparted by the fact that the moieties R, Z and Z' can be varied as well, thereby providing added control over the physiochemical properties of the desired compound.

Preferred growth hormone releasing compounds employed in the practice of the present invention are selected from the group consisting of:

His—Ala—AA2—Ala—Trp—AA5—AAT—NH$_2$,

His—Ala—AA2—Ala—Trp—AA5—AA6—AA7—NH$_2$, and organic or inorganic addition salts of any of said polypeptides; any of which can optionally be preceded by AA0; where AA0, AA2, AA5, AA6 and AA7 are as defined above.

These compounds are preferred because of their ease of synthesis, proven efficacy at promoting an increase in serum growth hormone levels, and their consequent appeal for commercial scale production and utilization. In addition, these compounds may be advantageous in having physiochemical properties which are desirable for the efficient delivery of such polypeptide compounds to a variety of animal species. Because of the flexibility made possible by the various substitutions at numerous positions of the invention polypeptide compounds, a wide range of delivery vehicles can be employed, by selecting the polar, neutral or non-polar nature of the N-terminal, C-terminal and center portions of these polypeptide compounds so as to be compatible with the desired method of delivery.

In a most preferred embodiment, the growth hormone releasing peptide employed in the practice of the present invention has the sequence:

His—Ala—AA2—Ala—Trp—AA5—AA7—NH$_2$;

or organic or inorganic addition salts thereof, where AA2, AA5 and AA7 are as defined above. A particularly preferred member of this most preferred group of compounds has the sequence:

His—Ala—DTrP—Ala—Trp—DPhe—Lys—NH$_2$, as well as organic or inorganic addition salts thereof.

These compounds are the presently most preferred because these shorter chain polypeptides are less expensive to synthesize, and these specific compounds have been shown to have a high level of potency at promoting the increase in serum growth hormone levels.

The compounds of this invention may be used to enhance blood GH levels in animals; enhance milk production in cows; enhance body growth in animals such as mammals (e.g., humans, sheep, bovines, and swine), as well as fish, fowl, other vertebrates and crustaceans; and increase wool and/or fur production in mammals. The amount of body growth is dependent upon the sex and age of the animal species, quantity and identity of the growth hormone releasing compound being administered, route of administration, and the like.

The novel polypeptide compounds of this invention can be synthesized according to the usual methods of solution and solid phase peptide chemistry, or by classical methods known in the art. The solid-phase synthesis is commenced from the C-terminal end of the peptide. A suitable starting material can be prepared, for instance, by attaching the required protected alpha-amino acid to a chloromethylated resin, a hydroxymethyl resin, a benzhydrylamine (BHA) resin, or a para-methyl-benzylhydrylamine (p-Me-BHA) resin. One such chloromethyl resin is sold under the tradename BIOBEADS SX-1 by Bio Rad Laboratories, Richmond, Calif. The preparation of the hydroxymethyl resin is described by Bodansky et al., Chem. Ind. (London) 38, 1597 (1966). The BHA resin has been described by Pietta and Marshall, Chem. Comm., 650 (1970) and is commercially available from Peninsula Laboratories, Inc., Belmont, Calif..

After the initial attachment, the alpha-amino protecting group can be removed by a choice of acidic reagents, including trifluoroacetic acid (TFA) or hydrochloric acid (HCl) solutions in organic solvents at room temperature. After removal of the alpha-amino protecting group, the remaining protected amino acids can be coupled stepwise in the desired order. Each protected amino acid can be generally reacted in about a 3-fold excess using an appropriate carboxyl group activator such sis dicyclohexylcarbodiimide (DCC) or diisopropyl carbodiimide (DIC) in solution, for example, in methylene chloride (CH$_2$Cl$_2$) or dimethylformamide (DMF) and mixtures thereof.

After the desired amino acid sequence has been completed, the desired peptide can be cleaved from the resin support by treatment with a reagent such as hydrogen fluoride (HF) which not only cleaves the peptide from the resin, but also cleaves most commonly used side-chain protecting groups. When a chloromethyl resin or hydroxymethyl resin is used, HF treatment results in the formation of the free peptide acid. When the BHA or p-Me-BHA resin is used, HF treatment results directly in free peptide amides.

The solid-phase procedure discussed above is well known in the art and has been described by Stewart and Young, *Solid Phase Peptide Synthesis*: Second Edn. (Pierce Chemical Co., Rockford, Ill., 1984).

Some of the well known solution methods which can be employed to synthesize the peptide moieties of the instant invention are set forth in Bodansky et al., *Peptide Synthesis*, 2nd Edition, John Wiley & Sons, New York, N.Y. 1976.

In accordance with another embodiment of the present invention, a method is provided for promoting release and/or elevation of growth hormone levels in the blood of an animal. Said method comprises administering to an animal an effective dose of at least one of the above-described polypeptides.

The compounds of this invention can be administered by oral, parenteral (intramuscular (i.m.), intraperitoneal (i.p.), intravenous (t.v.) or subcutaneous (s.c.) injection), nasal, vaginal, rectal or sublingual routes of administration and can be formulated in dose forms appropriate for each route of administration.

Solid dose forms for oral administration include capsules, tablets, pills, powders and granules. In such solid dose forms, the active compound is mixed with at least one inert carrier such as sucrose, lactose, or starch. Such dose forms can also comprise, as is normal practice, additional substances other than inert diluents, e.g., lubricating agents such as magnesium stearate. In the case of capsules, tablets and pills, the dose forms may also comprise buffering agents. Tablets and pills can additionally be prepared with enteric coatings.

Liquid dose forms for oral administration include emulsions, solutions, suspensions, syrups, the elixirs containing inert diluents commonly used in the art, such as water. Besides, such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dose forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in a medium of sterile water, or some other sterile injectable medium immediately before use.

As suggested in U.S. Pat. No. 4,880,778, incorporated by reference herein, the novel compounds of the present invention are also useful when administered in combination with growth hormone releasing hormone (i.e., naturally occurring growth hormone releasing hormone, analogs and functional equivalents thereof), as well as in combination with other compounds which promote the release of growth hormone, e.g., growth hormone releasing peptides. Such combinations represent an especially preferred means to administer the growth hormone releasing peptides of the present invention because the combination promotes the release of much more growth hormone than is predicted by the summation of the individual responses for each component of the combination, i.e., the combination provides a synergistic response relative to the individual component. For further detail on the administration of combinations of growth hormone releasing peptides, those of skill in the art are referred to the above-cited applications.

The amount of polypeptide or combination of polypeptides of the present invention administered will vary depending on numerous factors, e.g., the particular animal treated, its age and sex, the desired therapeutic affect, the route of administration and which polypeptide or combination of polypeptides are employed. In all instances, however, a dose effective to promote release and elevation of growth hormone level in the blood of the recipient animal is used. Ordinarily, this dose level falls in the range of between about 0.1 µg up to 10 mg of total polypeptide per kg of body weight. In general, the administration of combinations of growth hormone releasing peptides will allow for lower doses of the individual growth hormone releasing compounds to be employed relative to the dose levels required for individual growth hormone releasing compounds in order to obtain a similar response, due to the synergistic effect of the combination.

Also included within the scope of the present invention are compositions comprising, as an active ingredient, the organic and inorganic addition salts of the above described polypeptides and combinations thereof; optionally, in association with a carrier, diluents, slow release matrix, or coating.

The organic or inorganic addition salts of the growth hormone releasing compounds and combinations thereof contemplated to be within the scope of the present invention include salts of such organic moieties as acetate, trifluoroacetate, oxalate, valerate, oleate, laurate, benzoate, lactate, tosylate, citrate, maleate, fumarate, succinate, tartrate, naphthalate, and the like; and such inorganic moieties as Group I (i.e., alkali metal salts), Group II (i.e., alkaline earth metal salts) ammonium and protamine salts, zinc, iron, and the like with counterions such as the chloride, bromide, sulfate, phosphate and the like, as well as the organic moieties referred to above.

Pharmaceutically acceptable salts are preferred when administration to human subjects is contemplated. Such salts include the non-toxic alkali metal, alkaline earth metal and ammonium salts commonly used in the pharmaceutical industry including the sodium, potassium, lithium, calcium, magnesium, barium, ammonium and protamine salts which are prepared by methods well known in the art. The term also includes non-toxic acid addition salts which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

The invention will now be described in greater detail by reference to the following non-limiting examples.

EXAMPLE 1

Synthesis of the Growth Hormone Releasing Peptides

Paramethyl-benzhydrylamine hydrochloride (pMe—BHA.HCl) resin is placed in a reaction vessel on a commercially available automated peptide synthesizer. The resin is substituted with free amine up to a loading of about 5 mmoles per gram. The compounds are prepared by coupling individual amino acids starting at the carboxy terminus of the peptide sequence using an appropriate activing agent, such as N,N'-dicyclohexylcarbodiimide (DCC). The alpha amine of individual amino acids are protected, for example, as the t-butyloxycarbonyl derivative (t-Boc) and the reactive side chain functionalities are protected as outlined in Table 1.

TABLE 1

Side Chain Protecting Groups Suitable for Solid Phase Peptide Synthesis

| | |
|---|---|
| Arginine: | $N^g$-Tosyl |
| Aspartic Acid: | O-Benzyl |
| Cysteine: | S-para-Methylbenzyl |
| Glutamic Acid: | O-Benzyl |
| Histidine: | $N^{im}$-Tosyl |
| Lysine: | $N^\epsilon$-2,4-Dichlorobenzyloxycarbonyl |
| Methionine: | S-Sulfoxide |
| Serine: | O-Benzyl |
| Threonine: | O-Benzyl |
| Tryptophan: | $N^{in}$-Formyl |
| Tyrosine: | 0-2,6-Dichlorobenzyl |

Prior to incorporation of the initial amino acid, the resin is agitated three times (about one minute each) with dichloromethane ($CH_2Cl_2$; about 10 mL/gm of resin), neutralized with three agitations (about two minutes each) of N,N-diisopropylethylamine (DIEA) in dichloromethane (10:90; about 10 mL/gm of resin) and agitated three times (about one minute each) with dichloromethane (about 10 mL/gm of resin). The initial and each of the subsequent amino acids are coupled to the resin using a preformed symmetrical anhydride using about 3.0 times the total amount of the binding capacity of the resin of a suitably protected amino acid and about 1.5 times the total amount of the binding capacity of the resin of DCC in an appropriate amount of dichloromethane. For amino acids with a low dichloromethane solubility, N,N-dimethylformamide (DMF) is added to achieve a homogenous solution. Generally, the symmetrical anhydride is prepared up to 30 minutes prior to introduction into the reaction vessel at room temperature or below. The dicyclohexylurea that forms upon preparation of the symmetrical anhydride is removed via gravity filtration of the solution into the reaction vessel. Progress of the coupling of the amino acid to the resin is commonly monitored via a color test using a reagent such as ninhydrin (which reacts with primary and secondary amines. Upon complete coupling of the protected amino acid to the resin (>99%), the alpha amine protecting group is removed by treatment with acidic reagent(s). A commonly used reagent consists of a solution of trifluoroacetic acid (TFA), and anisole in dichloromethane (45:2:53). The complete procedure for incorporation of each individual amino acid residue onto the resin is outlined in Table 2.

TABLE 2

Procedure for Incorporation of Individual Amino Acids onto a Resin

| Reagent | Agitations | Time/Agitation |
|---|---|---|
| 1. Dichloromethane | 3 | 1 min. |
| 2. TFA, Anisole, Dichloromethane (45:2:53) | 1 | 2 min. |
| 3. TFA, Anisole, Dichloromethane (45:2:53) | 1 | 20 min. |
| 4. Dichloromethane | 3 | 1 min. |
| 5. DIEA, Dichloromethane (10:90) | 3 | 2 min. |

TABLE 2-continued

Procedure for Incorporation of Individual Amino Acids onto a Resin

| Reagent | Agitations | Time/Agitation |
|---|---|---|
| 6. Dichloromethane | 3 | 1 min. |
| 7. Preformed symmetrical anhydride | 1 | 15–120 min.* |
| 8. Dichloromethane | 3 | 1 min. |
| 9. iso-Propanol | 3 | 1 min. |
| 10. Dichloromethane | 3 | 1 min. |
| 11. Monitor progress of the coupling reaction** | | |
| 12. Repeat Steps 1–12 for each individual amino acid | | |

*Coupling time depends upon the individual amino acid.
**The extent of coupling can be generally monitored by a color test. If the coupling is incomplete, the same amino acid can be recoupled by repeating Steps 7–11. If the coupling is complete the next amino acid can be coupled.

By employing this method of peptide synthesis, novel resin-bound polypeptides such as:

are obtained (wherein X, AA2, AA3, AA5 and Y are as defined above, Ⓡ is a polymeric resin and functional groups of the constituent amino acids are protected with suitable protecting groups as needed). Specific sequences (in appropriately protected form) which conform to the above general formula and which can be prepared employing a variety of peptide-forming reactions include:

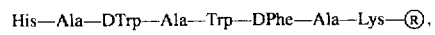

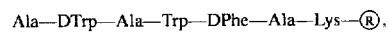

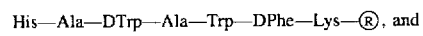

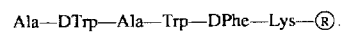

EXAMPLE 2

In Vivo GH Release in Rats

Immature female Sprague-Dawley rats were obtained from the Charles River Laboratories (Wilmington, Mass.). After arrival they were housed at 25° C. with a 14:10 hr light:dark cycle. Water and Purina rat chow were available ad libitum. Pups were kept with their mothers until 21 days of age.

Twenty-six day old rats, six rats per treatment group, were anesthetized interperitoneally with 50 mg/kg of pentobarbital 20 minute prior to i.v. treatment with peptide. Normal saline with 0.1% gelatin was the vehicle for intravenous (i.v.) injections of the peptides. The anesthetized rats, weighing 55–65 grams, were injected t.v. with the quantity of growth hormone releasing compounds indicated in Table 3. Injection was made as a 0.1 mL solution into the jugular vein.

All animals were sacrificed by guillotine 10 minutes after the final test injection (see Table 3). Trunk blood for the determination of blood GH levels was collected following decapitation. After allowing the blood to clot, it was centrifuged and the serum was separated from the clot. Serum was kept frozen until the day of sampling for radioimmunoassay (RIA) determination of growth hormone levels according to the following procedure, as developed by the National Institute of Arthritis, Diabetes and Digestive and Kidney Diseases (NIADDK).

Reagents are generally added to the RIA analysis tubes at a single sitting, at refrigerator temperature (about 4° C.) in the following sequence:

(a) buffer, (b) "cold" (i.e., non-radioactive) standard or unknown serum sample to be analyzed, (c) radio-iodinated growth hormone antigen, and (d) growth hormone antiserum.

Reagent addition is generally carried out so that there is achieved a final RIA tube dilution of about 1:30,000 (antiserum to total liquid volume; vol:vol).

The mixed reagents are then typically incubated at room temperature (about 25° C.) for about 24 hours prior to addition of a second antibody (e.g., goat or rabbit anti-monkey gamma globulin serum) which binds to and causes precipitation of the complexed growth hormone antiserum. Precipitated contents of the RIA tubes are then analyzed for the number of counts in a specified period of time in a gamma scintillation counter. A standard curve is prepared by plotting number of radioactive counts versus growth hormone (GH) level. GH levels of unknowns are then determined by reference to the standard curve.

Serum GH was measured by RIA with reagents provided by the National Hormone and Pituitary Program.

Serum levels in Table 3 are recorded in ng/mL in terms of the rat GH standard of 0.61 International Units/mg (IU/mg). Data is recorded as the mean +/− standard error of the mean (SEM). Statistical analysis was performed with Student's t-test. In Table 3 the results shown are the average of studies with six rats.

TABLE 3

In Vivo GH Release (ng/mL) Promoted by Growth Hormone Releasing Compounds in Pentobarbital Anesthetized Rats
(Animals Sacrificed 10 Minutes After Final Injection)

| Column A Growth Hormone Releasing Compounds | Total Dose (μg) | Control GH ng/mL | GH Released by Compound in Column A ng/mL |
|---|---|---|---|
| Ala—His—DTrp—Ala— Trp—DPhe—Lys—NH$_2$* | 0.1 | 287 ± 36 | 497 ± 88 |
|  | 0.3 | 287 ± 36 | 714 ± 57 |
|  | 1.0 | 287 ± 36 | 1422 ± 321 |
|  | 3.0 | 287 ± 36 | 1616 ± 418 |
| Lys—His—DTrp—Ala— Trp—DPhe—Lys—NH$_2$* | 0.1 | 287 ± 36 | 430 ± 89 |
|  | 0.3 | 287 ± 36 | 569 ± 106 |
|  | 1.0 | 287 ± 36 | 1561 ± 252 |
|  | 3.0 | 287 ± 36 | 2303 ± 104 |
| His—Ala—DTrp—Ala— Trp—DPhe—Lys—NH$_2$ | 3.0 | 111 ± 25 | 2588 ± 341 |
| His—Ser—DTrp—Ala— Trp—DPhe—Lys—NH$_2$ | 1.0 | 220 ± 29 | 389 ± 146 |
|  | 10.0 | 220 ± 29 | 1458 ± 277 |
|  | 30.0 | 220 ± 29 | 5716 ± 211 |
|  | 10.0 | 239 ± 36 | 1420 ± 222 |
|  | 30.0 | 239 ± 36 | 3292 ± 474 |
| His—Gln—DTrp—Ala— Trp—DPhe—Lys—NH$_2$ | 1.0 | 220 ± 29 | 693 ± 245 |
|  | 10.0 | 220 ± 20 | 373 ± 75 |
|  | 30.0 | 220 ± 29 | 832 ± 148 |
| His—Leu—DTrp—Ala— Trp—DPhe—Lys—NH$_2$ | 0.1 | 239 ± 36 | 292 ± 19 |
|  | 0.3 | 239 ± 36 | 466 ± 70 |
|  | 1.0 | 239 ± 36 | 369 ± 59 |
|  | 3.0 | 239 ± 36 | 426 ± 88 |
| His—DAla—DTrp—Ala— Trp—DPhe—Lys—NH$_2$ | 0.1 | 239 ± 36 | 296 ± 49 |
|  | 0.3 | 239 ± 36 | 241 ± 26 |
|  | 1.0 | 239 ± 36 | 470 ± 105 |

TABLE 3-continued

In Vivo GH Release (ng/mL) Promoted by Growth Hormone Releasing Compounds in Pentobarbital Anesthetized Rats
(Animals Sacrificed 10 Minutes After Final Injection)

| Column A Growth Hormone Releasing Compounds | Total Dose (μg) | Control GH ng/mL | GH Released by Compound in Column A ng/mL |
|---|---|---|---|
|  | 3.0 | 239 ± 36 | 402 ± 64 |
| His—Asp—DTrp—Ala— Trp—DPhe—Lys—NH$_2$ | 0.1 | 239 ± 36 | 263 ± 54 |
|  | 0.3 | 239 ± 36 | 228 ± 105 |
|  | 1.0 | 239 ± 36 | 309 ± 38 |
|  | 3.0 | 239 ± 36 | 298 ± 50 |
| His—Pro—DTrp—Ala— Trp—DPhe—Lys—NH$_2$ | 0.1 | 239 ± 36 | 406 ± 40 |
|  | 0.3 | 239 ± 36 | 334 ± 26 |
|  | 1.0 | 239 ± 36 | 258 ± 29 |
|  | 3.0 | 239 ± 36 | 294 ± 64 |

*Comparison Peptides

In Table 3, compounds of the invention are shown to promote the release and elevation of growth hormone levels in the blood of rats to which such compounds have been administered.

EXAMPLE 3

Administration of a Combination of GH-Releasing Compounds

The procedure of Example 2 was repeated, except the rats were not anesthetized nor were they pretreated with pentobarbital, and a combination of peptides were administered to the rats. The compounds administered, the dose levels and results are set forth in Table 4.

TABLE 4

In Vivo Synergistic Effects in Unanesthetized Rats of Invention Compound with Group 1* and/or Group 3* Compounds

| Compound Administered; Dose (μg)* | GH Released, mg/mL |
|---|---|
| Control | 12 ± 3 |
| Invention Compound, 10 | 111 ± 26 |
| Comparison Compound, 10 | 204 ± 51 |
| Group 1 Compound, 3 | 131 ± 50 |
| Invention + Group 1 | 1976 ± 714 |
| Comparison + Group 1 | 2525 ± 453 |
| Group 3 Compound, 10 | 79 ± 29 |
| Invention + Group 3 | 1271 ± 394 |
| Comparison + Group 3 | 1597 ± 387 |
| Invention + Group 1 + Group 3 | 4622 ± 517 |
| Comparison + Group 1 + Group 3 | 4344 ± 374 |

*Group 1 and Group 3 compounds are described in detail in U.S. Pat. No. 4,880,778, which has been incorporated by reference herein. All compounds employed in these studies have the following sequences:
Invention Compound -
His—Ala—DTrp—Ala—Trp—DPhe—Lys—NH$_2$;
Comparision Compound -
His—DTrp—Ala—Trp—DPhe—Lys—NH$_2$;
Group 1 Compound -
Tyr—Ala—Asp—Ala—Ile—Phe—Thr—Asn—Ser—Tyr—Arg—Lys—Val—Leu—Gly—Gln—Leu—Ser—Ala—Arg—Lys—Leu—Leu—Gln—Asp—Ile—Nle—Ser—Arg—NH$_2$;
Group 3 Compound -
Tyr—DArg—Phe—Gly—NH$_2$ The results in Table 4 demonstrate that invention compound displays a similar synergistic response to that obtained with comparison compound (which has previously been shown to give a synergistic response) when administered in combination with exemplary Group 1 and/or Group 3 compounds.

EXAMPLE 4

In Vivo Growth Hormone Release Study—Cows

Six multiparous lactating Holstein cows (mean body weight 575 kg) were housed in a dairy barn. The cow diet consisted of a forage to concentrate ratio of 50:50 with 70% of the forage dry matter as corn silage and 30% as alfalfa hay. The concentrate portion of the diet contained corn and soybean meal in adequate quantities to provide a total mixed ration. The ration was balanced following NRC guidelines to meet the nutrient requirements (i.e., dry matter, protein, energy, crude fiber, minerals and vitamins) of dairy cows in early to mid-lactation. Cows were fed twice daily.

Catheters were inserted into the Jugular vein for withdrawal of blood samples and i.v. injections of peptides. Approximately 4 mL of saline was flushed through the catheter after each blood drawing. Six mL blood samples were collected between about 12:20 pm and 4 pm at −40, −20, −10, 0, +5, +10, +15, +20, +30, +40, +60, +80, +100, +140, and +160 minutes, on each day of the study. Normal saline or peptides dissolved in normal saline was injected i.v. through the catheter at 0 time to the unanesthetized cows. The saline/peptide was infused bolus (5.0 mL volume). The blood was collected in EDTA treated tubes, centrifuged and the plasma separated from the pellet. Plasma was kept frozen until the day of sampling for radioimmunoassay (RIA) of growth hormone. Plasma GH was measured by RIA with reagents provided by the NIADDK. The GH levels are reported in terms of ng/mL of a bovine GH reference preparation, NIH-GH-B18, which is equivalent to 3.2 IU/mg. Data is recorded as the mean± the standard error of the mean (SEM). Statistical analysis was performed with the Student's t-test. Results are presented in Table 5.

TABLE 5

Relative Potencies of His—DTrp—Ala—Trp—DPhe—
Lys—NH$_2$ (Comparison A), Lys—His—DTrp—Ala—Trp—
DPhe—Lys—NH$_2$ (Comparison B), and
His—Ala—DTrp—Ala—Trp—DPhe—Lys—NH$_2$
(Invention) in Lactating Dairy Cows

| Compounds | 3 mcg/kg Body Weight | | 9 mcg/kg Body Weight | |
|---|---|---|---|---|
| | GH AUC* ng-min/ mL | Log (GH AUC) | GH AUC ng-min/ mL | Log (GH AUC) |
| Comparison A | 1,485 ± 1,008 | 6.86 ± 0.38 | 3,734 ± 1,008 | 7.82 ± 0.38 |
| Comparison B | 795 ± 1,008 | 6.72 ± 0.38 | 3,129 ± 1,008 | 7.81 ± 0.38 |
| Invention | 1,107 ± 1,008 | 6.11 ± 0.42 | 2,431 ± 1,008 | 7.04 ± 0.38 |

*GH AUC is GH area under the curve over 180 min after bolus I.V. infusion; all GH values were corrected for differences in molecular weights of each compounds.

In Table 5, invention compound is shown to promote the release and elevation of growth hormone levels in the blood of lactating dairy cows to which the compound has been administered. The level of growth hormone release observed in greater than or equal to the levels observed with previously disclosed novel growth hormone releasing peptides.

The invention has been described in detail with particular reference to preferred embodiments thereof, but it will be understood that variations and modifications can be effected within the spirit and scope of the invention.

We claim:

1. A polypeptide which promotes the release and elevation of growth hormone levels in the blood of a recipient animal, wherein said polypeptide is selected from the group consisting of polypeptides having the generic structure:

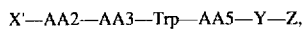

X'—AA2—AA3—Trp—AA5—Y—Z, wherein X' is selected from the group consisting of His— AA1'—, 3(NMe)His—AA1'—, AA0—His—AA1', and AA0—3(NMe)His—AA1'; wherein AA0 is selected from the group consisting of all naturally occurring L-amino acids, Met(O), DOPA and Abu; and AA1' is selected from the group consisting of Ala, Ser, Gln, Leu, Pro, and DAla, AA2 is selected from the group consisting of DPhe, DTrp, 5-fluoro-DTrp, 5-fluoro-Trp, 6-fluoro-DTrp, 6-fluoro-Trp, (formyl)DTrp, and ,XTrp, wherein ,XTrp is selected from the group consisting of (N$^\alpha$Me)DTrp, (indole NMe)DTrp, D$^\alpha$Nal and D$^\beta$Nal;

AA3 is selected from the group consisting of Ala, Gly and Ser;

AA5 is selected from the group consisting of DPhe and (NMe)DPhe;

Y is AA7, wherein AA7 is selected from the group consisting of Arg, iLys, Lys and Orn; and Z represents the C terminal end group of said polypeptide, the C terminal amino acid plus end group, or the C terminal amino acids plus end group wherein Z is selected from the group consisting of —CONH$_2$, —COOH, —COOR, —CONHR, —CONR$_2$, —CH$_2$OH, —CH$_2$OR, —Gly—Z', —Met—Z', —Lys—Z', —Cys—Z', —Gly—Tyr—Z', and —Ala— Tyr—Z', wherein Z' is selected from the group consisting of —CONH$_2$, —COOH, —CONHR, —COOR, —CONR$_2$, —CH$_2$OH, and —CH$_2$OR, wherein R is an alkyl group having 1–6 carbon atoms or an aromatic ring having up to 12 carbon atoms;

or organic or inorganic addition salts of any of said polypeptides;

wherein all three letter amino acid abbreviations preceded by a "D" indicate the D-configuration of the amino acid residue; and glycine is included in the scope of the term "naturally occurring L-amino acids".

2. A polypeptide in accordance with claim 1 wherein said polypeptide has the sequence:

His—Ala—AA2—Ala—Trp—AA5—AA7—NH2, or organic or inorganic addition salts thereof, wherein AA2, AA5 and AA7 are as defined above.

3. A polypeptide having the sequence:

His—Ala—DTrp—Ala—TrTp—DPhe—Lys—NH2; or organic or inorganic addition salts thereof.

4. The polypeptide of claim 1, wherein AA2 is DTrp.

5. A method of promoting the release and elevation of blood growth hormone levels in an animal which comprises administering to the animal in need of the treatment a therapeutically effective amount of the polypeptide set forth in claim 2.

6. A method of promoting the release and elevation of blood growth hormone levels in an animal which comprises administering to the animal in need of the treatment a therapeutically effective amount of the polypeptide set forth in claim 3.

7. A method of promoting the release and elevation of blood growth hormone levels in a mammal, which comprises administering to the mammal in need of the treatment an effective amount of the polypeptide of claim 1.

8. The method of claim 7, wherein the polypeptide has the sequence His—Ala—AA2—Ala—Trp—AA5—AA7—NH$_2$ or organic of inorganic addition salts thereof.

9. The method of claim 8, wherein AA2 is DTrp.

* * * * *